United States Patent
Lozano

(10) Patent No.: US 7,285,118 B1
(45) Date of Patent: Oct. 23, 2007

(54) BRAIN STIMULATION LEAD USED FOR LESIONING

(75) Inventor: Andres M. Lozano, Toronto (CA)

(73) Assignee: Functional Neuroscience Inc., Toronto (CA)

( * ) Notice: Subject to any disclaimer, the term of this patent is extended or adjusted under 35 U.S.C. 154(b) by 462 days.

(21) Appl. No.: 10/622,227

(22) Filed: Jul. 18, 2003

Related U.S. Application Data

(60) Provisional application No. 60/397,086, filed on Jul. 18, 2002.

(51) Int. Cl.
A61B 18/18 (2006.01)
(52) U.S. Cl. .................. 606/41; 607/116; 128/898; 600/378
(58) Field of Classification Search ........... 607/115, 607/116, 117, 122, 123, 148; 600/372, 373, 600/393, 378; 128/898
See application file for complete search history.

(56) References Cited

U.S. PATENT DOCUMENTS

| | | | |
|---|---|---|---|
| 4,907,589 A * | 3/1990 | Cosman | 606/34 |
| 5,832,932 A | 11/1998 | Elsberry et al. | |
| 6,094,598 A | 7/2000 | Elsberry et al. | |
| 6,356,784 B1 | 3/2002 | Lozano et al. | |
| 2002/0013612 A1 | 1/2002 | Whitehurst | |
| 2003/0083724 A1 | 5/2003 | Jog et al. | |

FOREIGN PATENT DOCUMENTS

WO WO-02/068042 A1 9/2002

OTHER PUBLICATIONS

IPCOM000010695D, "Stimulation Leads with Radial and Longitudinal Steerability", (published: Jan. 9, 2003), 6 pages.

Bertram, et al., "Design and Construction of a Long-Term Continuous Video-EEG Monitoring Unit for Simultaneous Recording of Multiple Small Animals", Brain Research Brain Research Protocols, vol. 2(1), (Dec. 1, 1997), pp. 85-97.

Burgess RC., "Design and Evolution of a System for Long-Term Electroencephalographic and Video Monitoring of Epilepsy Patients", Methods, vol. 2 Review, (Oct. 25, 2001), pp. 231-248.

Ives, et al., "128-channel Cable-Telemetry EEG Recording System for Long-Term Invasive Monitoring", Electroencephalogr Clin Neurophysiol, vol. 79(1), (Jul. 1991), pp. 69-72.

(Continued)

Primary Examiner—Michael Peffley
(74) Attorney, Agent, or Firm—Laura Haburay Bishop

(57) ABSTRACT

A brain stimulation lead such as a deep brain stimulation (DBS) lead is provided, which lead can also be used to create lesions safely and effectively due to inclusion of temperature sensing. The generating of radio-frequency (RF) lesions via a brain stimulation lead provides a new treatment option, for instance, when hardware-related or other complications necessitate lead removal. An existing implanted DBS lead was used to create lesions in the thalamus and subthalamus of patients with movement disorders. Various brain stimulation leads with temperature sensors are described. Various methods are disclosed, including creation of a lesion with a brain stimulation lead while sensing temperature with a sensor implanted as part of the lead or with a noninvasive sensing device. Another method includes creating a graduated lesion with a brain stimulation lead of the invention or with a chronic lesioning lead.

19 Claims, 9 Drawing Sheets

OTHER PUBLICATIONS

Kumar, et al., "Radiofrequency Lesioning Through an Implanted Deep Brain Stimulating Electrode: Treatment of Tolerance to Thalamic Stimulation in Essential Tremor", Movement Disorders, vol. 15, Suppl. 3, (2000) p. 69.

Oh, et al., "Deep Brain Stimulator Electrodes Used for Lesioning: Proof of Principle", Neurosurgy, vol. 49, No. 2, (Aug. 2001) pp. 363-369.

Scott, et al., "Design of an Intensive Epilepsy Monitoring Unit", Epilepsia, vol. 41, Suppl. 5, (2000) pp. S3-S8.

Raoul, et al., "Staged Lesions Through Implanted Deep Brain Stimulating Electrodes: A New Surgical Procedure for Treating Tremor or Dyskinesia", Abstracts of the Movement Disorder Society's 7th International Congree of Parkinson's Disease and Movement Disorders, held Nov. 10-14, 2002, Miami Florida, published in Movement Disorders, vol. 17, Suppl. 5 (2002), cover page, p. S210, and enlarged relevant section of p. S210.

Raoul, et al., "Staged Lesions Through Implanted Deep Brain Stimulating Electrodes: A New Surgical Procedure for Treating Tremor or Dyskinesias", Movement Disorders, vol. 18, Issue 8, (2003), pp. 933-938.

Raoul, et al., "Lesions using DBS Electrodes: Experimental Studies in Fresh Egg Whites and in Human Cadavers", Abstract of Presentation to American Society for Stereotactic and Functional Neurosurgery, held May 18-21, 2003, New York City, cover page and p. 162.

* cited by examiner

BRAIN STIMULATION LEAD USED FOR LESIONING

The present application claims the benefit of U.S. Provisional Patent Application Ser. No. 60/397,086, filed Jul. 18, 2002, which application is incorporated herein by reference in its entirety.

FIELD OF THE INVENTION

The present invention generally relates to brain treatment methods and systems, and more particularly, to brain stimulation leads or electrodes used for both stimulation and lesioning.

BACKGROUND OF THE INVENTION

Chronic deep brain stimulation (DBS) is becoming an established neuro-surgical procedure in the treatment of movement disorders, and is now often used in place of the conventional approach of lesioning or ablation. DBS typically entails chronic implantation of a stimulating electrode (referred to herein as a lead) specially designed to apply energy from a pulse generator that is implanted beneath the skin. Ablative procedures (a.k.a., lesioning) typically involve acute insertion of a lead specially designed to apply energy from an external radio-frequency (RF) generator. Lesioning and DBS have similar efficacy in the treatment of movement disorders. While lesioning causes permanent destruction of the target cells, DBS reversibly inhibits or excites cells.

When compared with ablative procedures, DBS seems to have an improved side effect profile. As with any implanted system, DBS therapy involves certain issues related to the therapy and to the DBS hardware. Patients with chronically implanted DBS leads can encounter complications requiring hardware revision or removal. For instance, DBS devices can introduce infection, erode through the skin, fracture, migrate, short-circuit, or physically disconnect. In some instances, e.g., of skin erosion or infection, the DBS lead may need to be removed even though it continues to produce important clinical benefits.

When the DBS or other brain stimulation lead is removed, patients experience loss of therapeutic benefit and increased disability. Generally after a time delay, surgical options may include either repeated lead implantation or a lesioning procedure. Another scenario in which lesioning may be considered occurs in patients who develop a tolerance to stimulation, such as those with essential tremor who develop a tolerance to DBS, and therefore lose therapeutic effectiveness. Data shows that up to 50% of DBS patients with essential tremor develop a tolerance to DBS. Such patients may require progressively increasing current output for treatment (e.g., tremor suppression), leading to battery failure and/or frequent and impractical battery replacements.

It has been suggested to use a DBS lead for lesioning. See, for instance, Kumar, et al., "RF Lesioning through an Implanted Deep Brain Stimulating Electrode Treatment of Tolerance to Thalamic Stimulation in Essential Tremor" *Movement Disorders* 2000;15 Suppl 3:69. However, there are several problems with the approach described. For instance, the authors indicate that the RF parameters required to create the lesion were determined using egg white. While this is indicative of appropriate parameters, a more definite approach would be beneficial. Furthermore, the authors state that "RF lesioning can be safely performed through an implanted DBS electrode. This is an effective treatment . . . " The efficacy of the procedure is questionable without feedback that ensures the temperature reaches that required to create the lesion(s), while the safety of the procedure is questionable without feedback that ensures the temperature does not exceed that required to create the lesion(s), which could cause destruction of cells in a larger area than desired during the procedure.

A similar approach to lesion creation with a DBS electrode was described in an article of the present inventor and his associates. See Oh, et al., "Deep Brain Stimulator Electrodes Used for Lesioning: Proof of Principle" *Neurosurgery* 2001 August; 49(2):363-369. As pointed out by the authors, "temperature measurement is not available when using a DBS electrode for RF lesion generation." Filed shortly after publication of the Oh, et al. article, US Patent Application 2003/0083724 A1 describes a specific configuration of multichannel electrode, designed to perform recording, stimulating, and lesioning. It may further provide imaging capability and/or therapies such as drug or radiation delivery. Yet again, the described device lacks the capacity to measure temperature, limiting the efficacy and safety of procedures using the device.

SUMMARY OF THE INVENTION

The present invention addresses the above and other needs by providing brain stimulation leads and methods that can also be used to create lesions effectively and safely. The leads and methods of the invention incorporate means for sensing temperature during lesioning, which allows real-time monitoring, fail-safe features, or even closed-loop control over the lesioning process.

Various embodiments include additional capabilities, such as infusion and/or microelectrode-type recording via the lead. The leads of the invention may be used to create a lesion in a single session, or to create progressive, graduated or incremental lesions, inside or outside the operating room. Generation of radio-frequency (RF) lesions via the electrodes and methods of the invention provides a new, simpler treatment option when hardware-related or other complications necessitate lead removal or revision.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
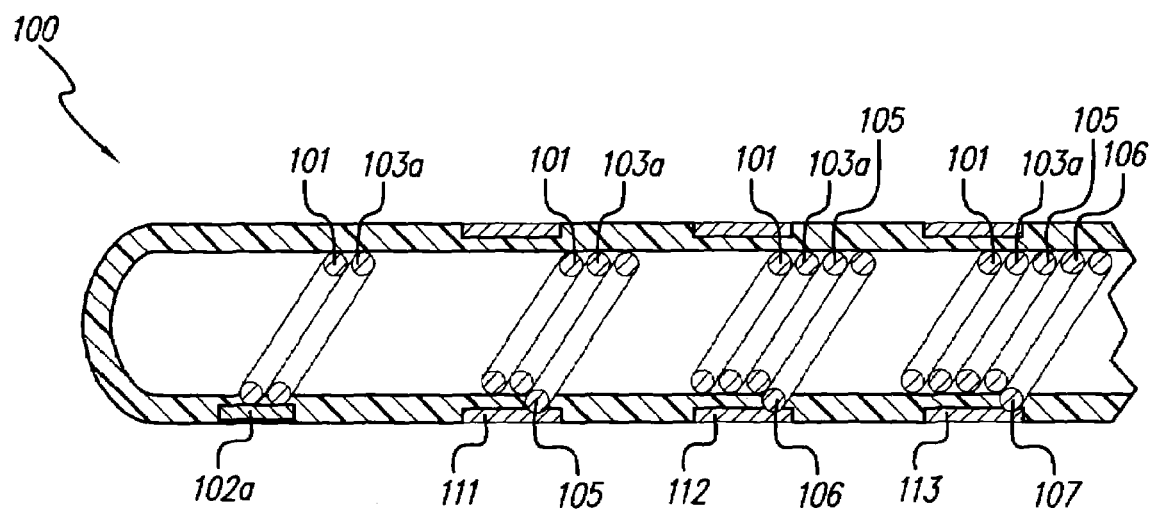
FIG. 1 is an axial cross-section view of the distal end of a lead of the present invention, with a temperature sensor positioned on the surface of the lead, near the distal tip.

The following description is of the best mode presently contemplated for carrying out the invention. This description is not to be taken in a limiting sense, but is made merely for the purpose of describing the general principles of the invention. The scope of the invention should be determined with reference to the claims.

Although originally designed for neuroaugmentative purposes, a brain stimulation lead, such as a deep brain stimulation (DBS) lead, can be used to create lesions. The generating of radio-frequency (RF) lesions via a stimulation lead provides an additional treatment option when complications necessitate lead removal. Studies in egg whites and in two patients are described herein to illustrate systems and procedures involved.

In Vitro Studies

Before use in patients, the effects of RF current passed through a DBS lead were studied in fresh egg whites from hens to assess the safety and efficacy of using implanted DBS electrodes to create a therapeutic lesion before lead removal. (Egg whites were chosen as a medium because of their protein content and coagulation properties, and because their translucency allows easy visualization of lesions.) A series of studies were conducted to estimate the relationship between RF output parameters and lesion size using DBS electrodes inserted into the fresh egg whites. Both monopolar (between one DBS electrode and a ground) and bipolar (between, for instance, adjacent electrodes) configurations were evaluated; however, data for only the bipolar lesions, which were more reproducible, are described here.

On two separate dates, with the use of two DBS leads (one new and one that had been explanted), coagulation was studied. Approximately 200 ml of egg whites (12 eggs) in a square glass container was placed in a water bath warmed to 37 degrees Celsius. The distal ends of the leads were inserted into the egg whites until all four stimulating electrodes were completely immersed.

Various RF currents (0-125 mA) and two time durations were used. The frequency of the lesioning system was fixed at 100 KHz. Current was delivered for 60 or 90 seconds, as is common in clinical practice. Alligator clips were attached to adjacent contacts at the proximal end of the lead, corresponding to adjacent stimulating electrodes at the distal end of the lead, and each combination of current and time was repeated seven times for a total of 70 bipolar lesion trials. The impedance, electrode combination, current, voltage, and time were recorded for each bipolar lesion. Each coagulum was photographed, and the digital image was transferred to a photo editing program (Photoshop by Adobe Systems, Mountain View, Calif.). The coagulum size, as it appeared in the photograph, was measured (maximum width and length), and its shape was noted. The measurements were then corrected by reference to the known diameter of the leads. The mean and standard deviation of the lesions were calculated and tabulated. Statistical analysis was performed by using a two-way analysis of variance.

No coagulum was observed in egg whites at current outputs of 55 mA or less. At a setting of 75 mA, coagulum formed inconsistently (width ranged from zero to 4.8 mm and length ranged from zero to 6.4 mm) and often was irregular in shape (apple-, pear-, or dumbbell-shaped). At settings of 85 mA and 100 mA, coagulum was consistently formed (i.e., in 100% of trials). In these cases, coagulum usually developed as an ovoid opacification of the egg white and originated at both internal ends of the selected electrodes. The range of coagulum varied considerably: width ranged from 2.1 to 5.5 mm and length ranged from 2.2 to 7.2 mm. Reproducible lesions were obtained only at currents of 125 mA. At 125 mA, the borders were regular and well demarcated, and all were ovoid in shape with a mean width of $3.5 \pm 0.15$ mm and a mean length of $5.7 \pm 0.27$ mm. The mean impedance during the testing was $296 \pm 22$ ohms. The mean and standard deviation of coagulum size with current and time variables are shown in the table below.

| Current (mA) | Time (sec) | Width ± std dev (mm) | Length ± std dev (mm) |
|---|---|---|---|
| 75 | 60 | 2.0 ± 1.98 | 3.1 ± 2.99 |
| 85 | 60 | 3.5 ± 0.82 | 4.9 ± 1.76 |
| 100 | 60 | 3.4 ± 1.27 | 5.3 ± 1.69 |
| 125 | 60 | 3.6 ± 0.86 | 5.6 ± 0.44 |
| 75 | 90 | 3.1 ± 1.42 | 4.2 ± 1.93 |
| 85 | 90 | 3.6 ± 1.06 | 5.1 ± 1.22 |
| 100 | 90 | 3.9 ± 1.16 | 5.8 ± 0.86 |
| 125 | 90 | 3.5 ± 0.15 | 5.7 ± 0.27 |

In Vivo Studies

With the information above obtained from the in vitro studies, lesions were produced via implanted DBS leads in two patients. These two DBS patients were scheduled for either revision or removal of their DBS systems. One patient required frequent battery changes, and the other developed scalp erosion at the burr hole site through which the DBS lead entered the brain. Rather than complete removal or repeated revision of a sub-optimally functioning system, these individuals were offered the option (with approval of the ethics board of the Toronto Western Hospital) of using the existing DBS lead to create an RF lesion, and their informed consent was obtained before surgery.

The procedures were performed in the operating room with the patients under local anesthesia. The connector between the DBS lead (Model 3387 by Medtronic Sofamor Danek of Minneapolis, Minn., USA) and the lead extension, which lead extension courses from the scalp to the infraclavicular area where it connects to the internal pulse generator (IPG), was identified by palpation through the scalp. The connector was externalized via a 2 cm scalp incision, and the set screws were released to expose the four proximal contacts of the patient's existing DBS lead.

An OWL Universal RF generator (by Diros Technology of Toronto, Ontario, Canada) was used to generate the lesions. The frequency of the OWL RF generator is fixed at 100 KHz. To create a bipolar lesion, the RF generator's active and reference terminals were connected by alligator clips to two contiguous contacts on the DBS lead (corresponding to two adjacent electrodes). After generating the lesion, the DBS lead was reconnected to the lead extension cable and replaced in its subcutaneous location, and the incision was closed.

Patient 1

The first patient was a 51 year old man with essential tremor who had first received bilateral thalamic ventralis intermedius deep brain stimulation in 1995. He had very good tremor control after the procedure but over time developed tolerance, requiring increasing levels of stimulation for tremor control. Owing to the high voltage requirements, the left IPG was replaced in April 1998 and again one year later. Only three months later, the IPG battery was again depleted. At this time, the patient's stimulation settings were amplitude 6.3 V, pulse width 210 µs, and frequency 185 Hz. Without stimulation, the tremor was graded on the right upper extremity as 2/4 at rest, 3/4 with arms extended, and 3/4 with finger-to-nose movement. With DBS, the corresponding scores were 0/4, 1/4, and 1/4.

Simply replacing the battery was deemed unsatisfactory because battery changes would be required too frequently. The options considered included 1) replacing the IPG with an RF receiver activated through an external generator, 2) performing a left stereotactic thalamotomy, or 3) using the existing DBS lead to create a lesion. The patient chose the lesion option.

With the patient under local anesthesia, the proximal end of the patient's brain stimulation lead was externalized, as described above. Using an external pulse generator and the patient's most recent settings (electrode 1 negative, adjacent electrode 2 positive, frequency 185 Hz, pulse width 210 µs), tremor arrest was obtained at 3 V (after a stimulation reprieve of three weeks) without additional associated neurological symptoms.

On the basis of this clinical response, a bipolar lesion was created using electrodes 1 and 2 as the active and reference electrodes, respectively. An impedance of 700 ohms was measured. The current passed through the lead was increased from 25 mA to 45 mA for 60 seconds without any reported or observed clinical or adverse effect. At 75 mA (30 V) for 60 seconds (impedance of 600 ohms), a significant reduction in tremor was noted and the patient reported mild, transient numbness of the tongue and right perilabial area. The current was increased to 90 mA (31 V), and tremor arrest was noted after 60 seconds.

After lesioning, mild contralateral tongue and perioral numbness was reported by the patient. The lead was then reconnected to the lead extension, the connector was replaced under the scalp, and the scalp incision was closed. The lead was left in place for possible future repeat lesioning or reinstating the stimulation after lesioning.

Magnetic resonance imaging (MRI) performed one day after lesioning demonstrated a signal change around the lead in the left thalamus, with some edema extending into the posterior limb of the internal capsule. The patient was examined at three and six months after lesioning with the brain stimulation lead. At the six-month follow-up examination, with DBS stimulation off, the patient continued to have excellent tremor control, rated 0/4 at rest, 2/4 with arms outstretched, and 1/4 with finger-to-nose movement. Spiral drawings obtained before and after lesioning through the brain stimulation lead (and with stimulation off) also demonstrated the effectiveness of the thalamotomy on the patient's handwriting. Tongue numbness was minimal three months after the procedure and no longer present six months after the procedure.

Patient 2

A 59 year old man with Parkinson's disease underwent bilateral subthalamic nucleus DBS implantation in January 2000. He had an excellent response to DBS: improved motor fluctuations and resolved drug-induced dyskinesias. However, the hardware eroded the scalp at the cranial fixation site at the burr hole for the right DBS lead. The patient was offered the typical option of lead removal and replacement after four to six months. However, he was reluctant to have the DBS lead removed, as the stimulation provided significant benefits. On the basis of results with Patient 1, he was informed that a graduated lesion using the existing DBS lead was possible. The patient chose to proceed with the lesioning procedure. Removal of the hardware after lesioning was still an option.

The patient's preoperative settings were electrode 1 negative, adjacent electrode 2 negative, case positive, pulse width 90 µs, frequency 145 Hz. The proximal end of the right DBS lead was externalized and disconnected as described above. The RF generator was used for test stimulation by using electrode 1 as active and electrode 2 as reference. The measured impedance for this patient was 1500 ohms. At 3 V of stimulation, rigidity and bradykinesia of the left hand were improved. The patient also reported that he felt like laughing with stimulation.

A current of 25 mA (25 V) was passed for 60 seconds (impedance of 1400 ohms) between electrodes 1 and 2. During the trial lesion, the patient developed choreiform movements in the left foot and arm. Because of the development of these involuntary movements, no further lesions were made. The DBS lead was reconnected to the IPG and left in place. After debridement of the wound, primary wound closure was attempted. Owing to the uncertain long-term benefits of this small lesion and the patient's desire to retain the DBS lead, he received a rotation flap and split-thickness skin graft to cover the exposed hardware. Intravenous antibiotics were given for two weeks, followed by oral antibiotics for four weeks.

An immediate postoperative MRI scan showed a small amount of edema around the right DBS lead. The involuntary movements of the left leg resolved after three days, and the patient's clinical status as measured by the Unified Parkinson's Disease Rating Scale was unchanged postoperatively. No additional complications developed. Bilateral stimulation, including the right DBS lead that had been used for generating the RF lesion, was reinitiated.

At the three month follow-up examination, the patient had not taken any antibiotics for one month and the scalp was well healed. The patient reported that he had no dyskinesias and that he was falling less often, although the patient experienced difficulty for approximately 20% of each day. The patient's L-dopa dose had decreased by 40% and bromocriptine level had decreased by 65% compared with pre-stimulation doses.

For both patients, RF lesioning was started at 25 mA. Even this low intensity current is sufficient to produce a lesion, as supported by the clinical and MRI evidence for Patient 2. The lower threshold for lesion generation can be explained by the higher impedance measured in Patient 2 (1500 ohms) than in Patient 1 (700 ohms). This observation cautions for the use of low initial currents, particularly when a high level of impedance is found. The end point of lesioning in these patients was guided by their clinical response and the development of side effects. For both patients, lesions appeared as edema around the electrodes on postoperative MRI, and the DBS lead could still be used to deliver chronic electrical stimulation after lesioning. After the lesioning procedure, the patient with the subthalamic nucleus lead (Patient 2) resumed stimulation as before.

It is believed that the temperature of a lesioning electrode is directly related to lesion size. Thus, rather than using clinical response, development of side effects, and/or data from in vitro or other in vivo studies to determine the end point of lesioning, temperature may be used. Clinically, thermistor-coupled lesioning electrodes are typically used for creating RF lesions, and the temperature at the electrode during lesioning is typically monitored. However, temperature measurement is not available when using a standard brain stimulation lead, such as a standard DBS lead, for RF lesion generation. This may explain, at least in part, the variability in size and shape of lesions generated in the egg white experiments describe above.

The size of coagulum that formed had a tendency to increase with increasing RF current, but owing to the large dispersion around the mean, a consistent and reliable relationship was not established. Only at the highest RF current tested were lesions of reproducible size created. Additional factors that may lead to variability in coagulum shape and size include a change in impedance of the system or damage to the brain stimulation lead with repeated use for lesioning. These factors may lead to alterations or damage to electrode surface, which may contribute to the variability in coagulum size and shape.

The brain stimulation leads of the present invention include a temperature sensing device(s), enabling safe and effective lesioning of tissue adjacent electrodes of the leads. A variety of devices could be used to sense temperature, including but not limited to one or more thermistors, thermocouples, thermal transducers, resistance temperature detector (RTD) sensors, high-resistance lead thermometers, and/or optical-fiber probes using a variety of sensors, including birefringent and semiconductor crystals. For instance, a DBS lead, such as Model 3387 or 3389 by Medtronic, Inc. of Minneapolis, Minn. may be modified by the addition of a thermistor(s) and/or thermocouple(s) adjacent or attached to one or more electrodes.

Thus, the leads of the present invention are specifically manufactured to enable both electrical stimulation and lesioning with temperature sensing. For example, a lead with four electrodes along the distal portion of the lead may include a thermistor(s) and/or thermocouple(s) that senses temperature via a change in resistance and/or a change in junction voltage, respectively, and transmits the sensed temperature to an IPG or external generator via, for instance, a direct electrical connection.

Figure 2:
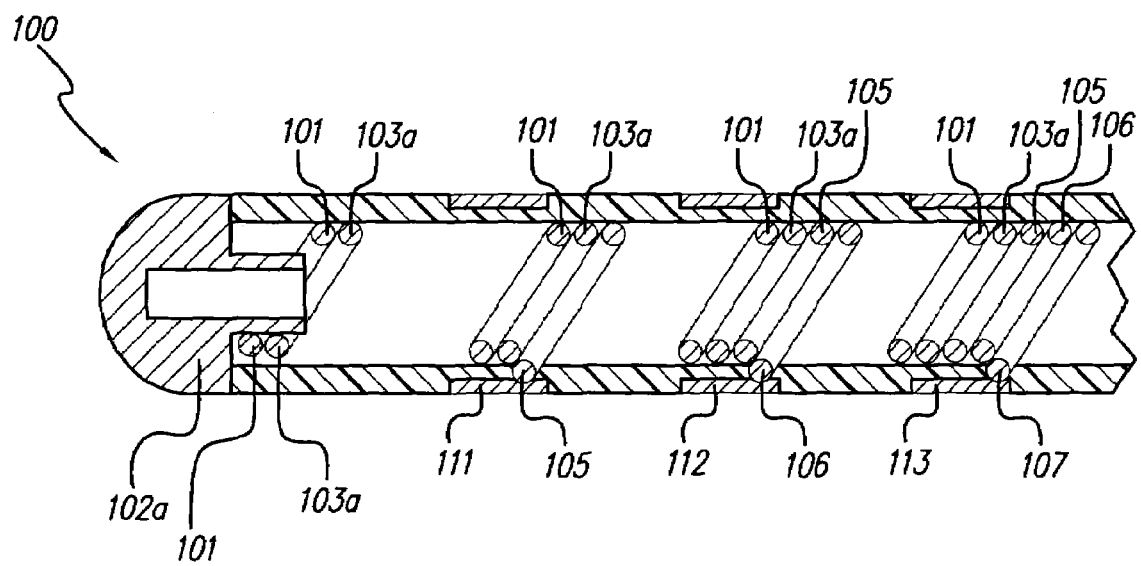
FIG. 2 is an axial cross-section view of the distal end of a lead of the present invention, with a temperature sensor at the distal tip.
Figure 3:
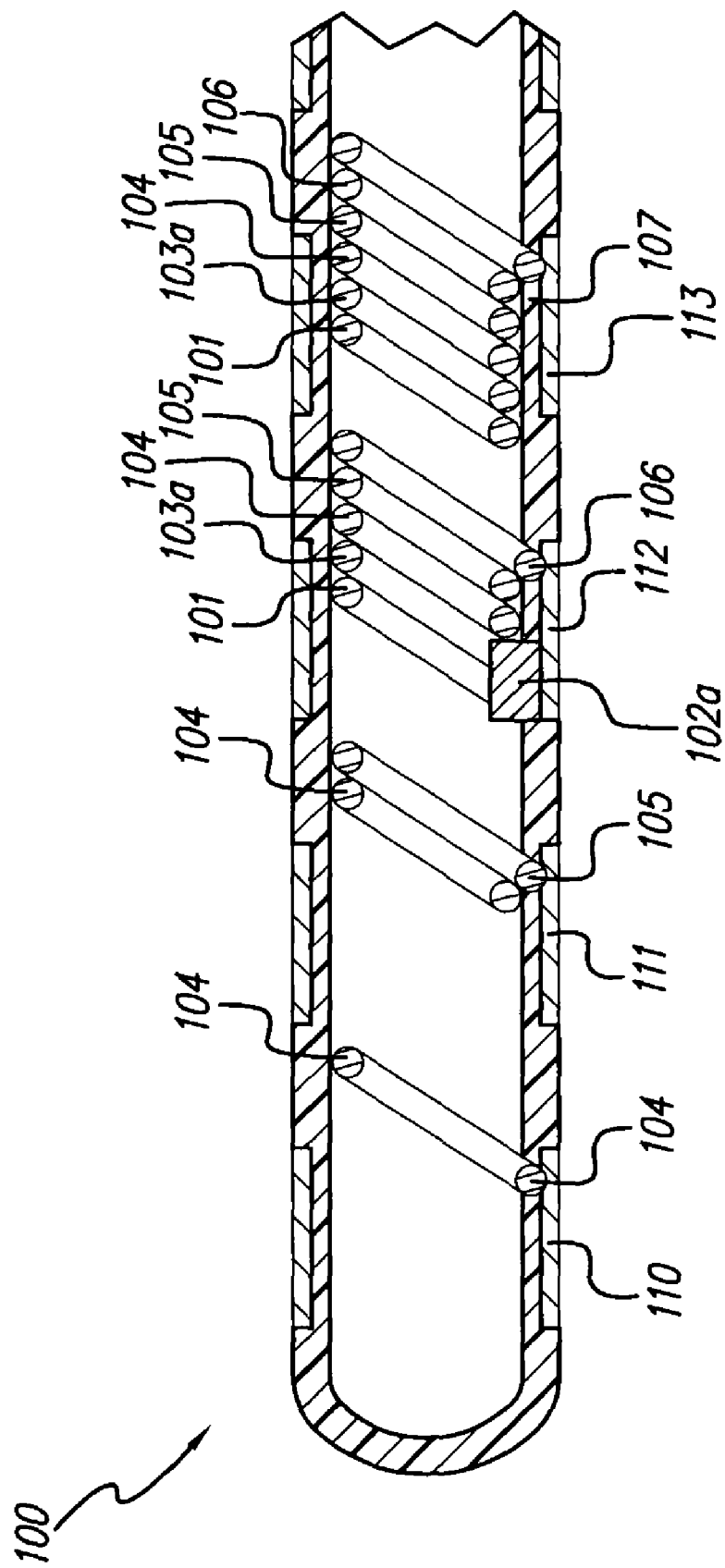
FIG. 3 is an axial cross-section view of the distal end of a lead of the present invention, showing a temperature sensor within the body of the lead.
Figure 4A:
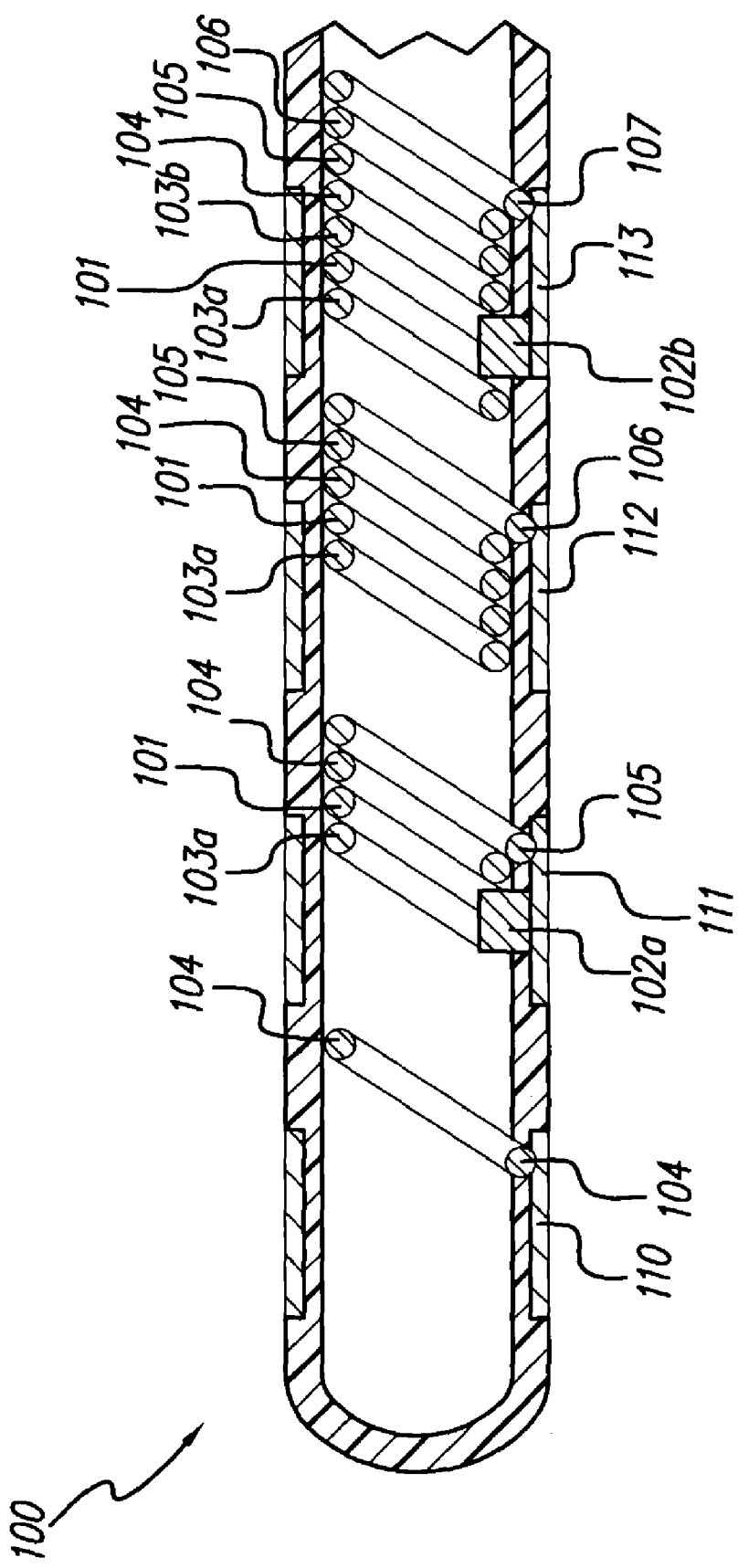
FIG. 4A shows, in axial cross-section view, the distal end of a lead of the present invention, showing multiple temperature sensors within the lead body.
Figure 4B:
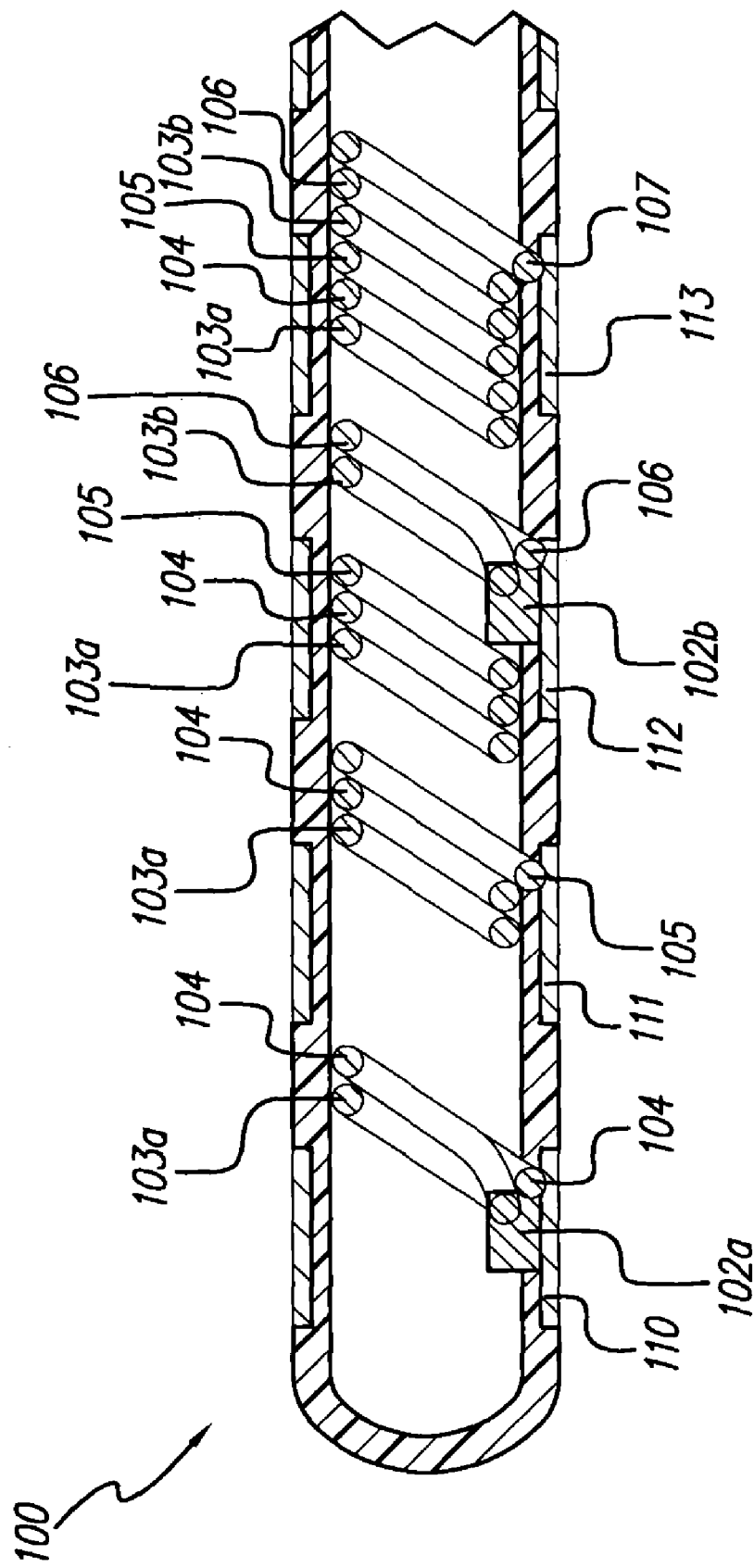
FIG. 4B shows, in axial cross-section view, the distal end of a lead of the present invention, showing an alternative method for electrically connecting temperature sensors.
Figure 5:
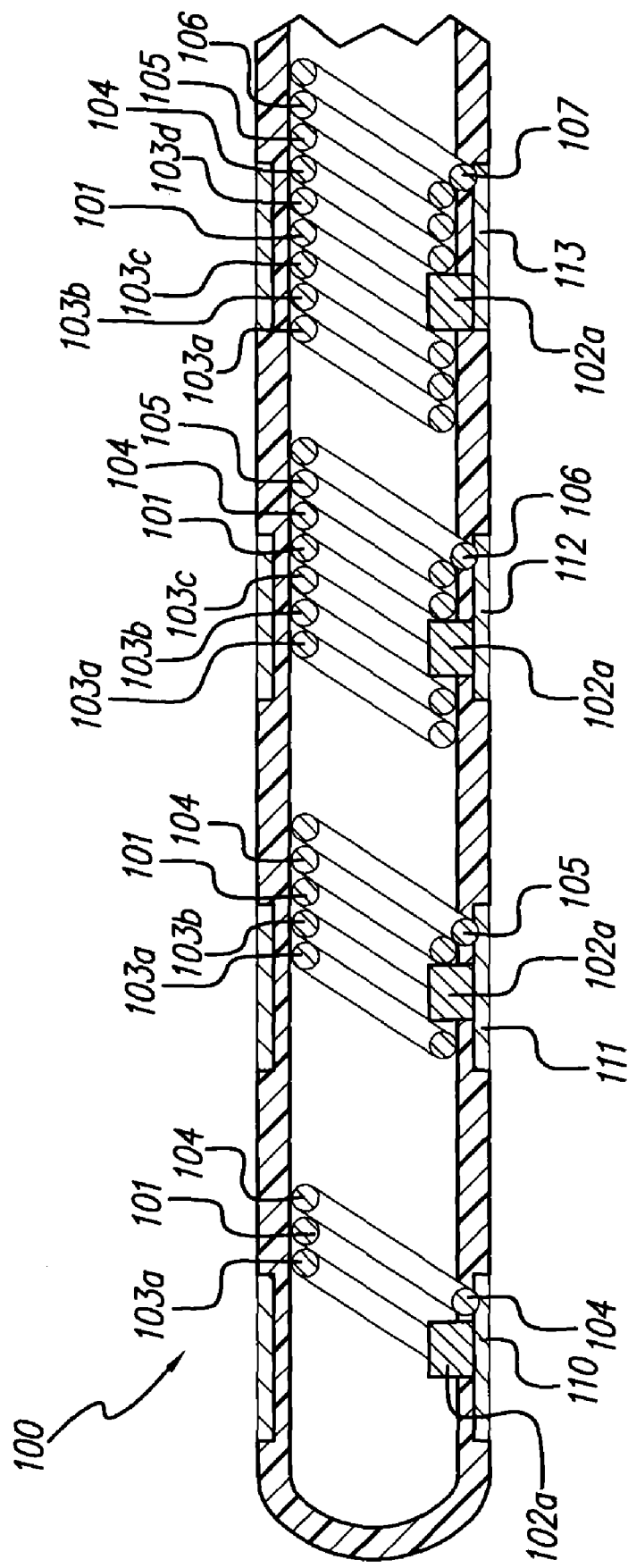
FIG. 5 is an axial cross-section view of the distal end of a lead of the present invention, showing multiple temperature sensors within the lead body.

FIGS. 1-5 are axial cross-section views of example leads 100 of the present invention. In FIGS. 1 and 2, conductors 105, 106, and 107 are electrically connected to electrodes 111, 112, and 113, respectively, at the distal end of lead 100. The conductors (a.k.a. wires) may be individually insulated wires constructed as a coil, as shown in the figures, may be cable conductors embedded in insulating material of the body of the lead, or other useful configuration. Thus, the wires/conductors are insulated, in any practical manner. In FIGS. 3-5, an additional insulated conductor 104 is electrically connected to an additional electrode 110. As is typical in the art, the conductors may extend proximally to contacts on the one or more connectors at the proximal end (not shown) of lead 100.

The stimulation that occurs at electrodes 110, 111, 112, and 113 is driven by a pulse generator electrically connected to the conductors and electrodes, e.g., via the connector(s) at the proximal end of lead 100. The pulse generator may be an implanted pulse generator or an external pulse generator. For instance, an external pulse generator may be attached to a connector(s) at the proximal end of lead 100, which lead may extend percutaneously to the stimulation site, or the pulse generator may communicate transcutaneously with an implanted RF receiver connected to the lead.

The lesioning that occurs at electrodes 110, 111, 112, and 113 is driven by an RF generator electrically connected to the conductors and electrodes. The RF generator may be, e.g., an OWL Universal RF generator, as described earlier, and may be electrically connected to the electrodes in a variety of ways. For instance, the RF generator may be directly connected to the lead via the connector(s) at the proximal end of lead 100. Alternatively, a needle(s) may be introduced through the scalp to make electrical connection with the implanted electrodes. In another alternative, the RF generator may be electrically connected to the electrodes via transcutaneous communication and powering with an implanted coil or receiver connected to the lead. In yet another alternative, the pulse generator may act as the RF generator when commanded, e.g., transcutaneously, to produce current to create a lesion.

The electrodes may be ring electrodes, as shown, or may be any other useful configuration. For instance, the electrodes may be sectioned and positioned around the outside of the lead as shown in publication number IPCOM000010695D, published Jan. 9, 2003 at IP.com and in the IP.com Journal, and incorporated herein by reference, or around a portion of the outside of the lead, as shown in International Application WO 02/068042, published Sep. 6, 2002, also incorporated herein by reference.

In FIGS. 1-3, two insulated wires, 101 (ground) and 103a, are electrically connected to temperature sensor 102a. In FIGS. 4A and 4B, multiple temperature sensors 102a and 102b are electrically connected to insulated sensor wires 103a and 103b, respectively. In FIG. 4A, each sensor 102 is also electrically connected to a common ground wire 101, while in FIG. 4B, the electrode wires 104 and 106 also function as wires for the temperature sensors. The temperature at the sensor may thus be determined via the voltage measured between the two wires attached to the sensor. In FIG. 5, multiple temperature sensors 102a, 102b, 102c, and 102d, are electrically connected to insulated sensor wires 103a, 103b, 103c, and 103d, respectively, and each sensor 102 is electrically connected to a common ground wire 101.

The sensor wires 103 also extend proximally to contacts on the one or more connectors at the proximal end (not shown) of lead 100. Signals from the sensors are delivered via electrical connection with the wires to the RF generator or separate temperature measurement circuit attached to the one or more connectors at the proximal end of lead 100. The temperature feedback allows real-time temperature monitoring during lesioning (or stimulation), use of safety (i.e., fail-safe) settings to limit lesioning parameters, and/or closed-loop control of lesioning parameters, as described below.

As is readily seen in the drawings, one or more sensors may be imbedded in the insulating material of the lead; may be flush with, situated on, or even protrude from the lead surface; or may be positioned in a lumen or other area of the lead. The sensor(s) may be at the tip of the lead, positioned between electrodes, positioned beside an electrode(s), or anywhere along or within the lead. For any of these cases, the sensor is described herein as "in" the lead. As will be appreciated by those of skill in the art, the example leads shown herein may be modified in numerous other ways and still be encompassed by the present invention.

Additionally or alternatively, noninvasive temperature sensing may be used with a brain stimulation lead that includes a sensor (for redundant, backup measurements) or with a standard brain stimulation lead, such as a standard DBS lead (which does not include a temperature sensor). For instance, ultrasound-computed tomography, which relies upon the change in the speed of sound versus temperature to determine internal tissue temperature at a particular location (s), may be used.

With temperature sensing included (internally or externally) with the brain stimulation system, lesion creation via current from the RF generator may not only be monitored (via real-time temperature monitoring), but may be controlled via closed-loop operation. For instance, with the lead attached to an RF generator, the clinician may set the desired lesioning temperature and time, and a controller will use the feedback from the temperature sensor(s) to apply sufficient energy from the RF generator to reach and keep the tissue at the desired temperature for the set amount of time. The controller may be a part of the RF generator, or may be a separate device electrically connected to the RF generator. The temperature may be measured while the RF energy is being applied. Alternatively, the RF energy may be attenuated or deactivated during periodic measurement of the temperature.

Currently, during implantation of a standard DBS system, a special recording microelectrode is inserted through a microelectrode cannula and slowly advanced until the target is identified. The microelectrode and cannula are then removed, and may be followed by insertion of a larger cannula and macroelectrode for testing prior to implantation of the chronic DBS electrode. Thus, multiple insertions and devices are used in a typical procedure.

In some embodiments, the brain stimulation lead of the invention includes recording capability. With this modification, the lead itself may be used to determine the target(s). Thus, a brain stimulation lead of the invention may be used for recording, stimulation, and effective and safe lesioning to treat disorders such as temporal lobe epilepsy.

For example, brain stimulation leads of the invention may initially be placed bilaterally in each temporal lobe for recording to determine the side and location from which most seizures arise. Once the location of the primary seizure focus is determined, a pulse generator may be attached to the lead to apply a stimulation waveform to that area. If stimulation is effective, the system may be implanted. If stimulation fails, is skipped, or is to follow creation of a lesion, RF energy may be directed through the lead to the primary seizure focus in order to produce a lesion in a controlled manner with temperature feedback. Lesioning prior to initiation or resumption of stimulation may decrease the current delivery requirements of stimulation, which may, inter alia, prolong battery life.

Figure 6A:
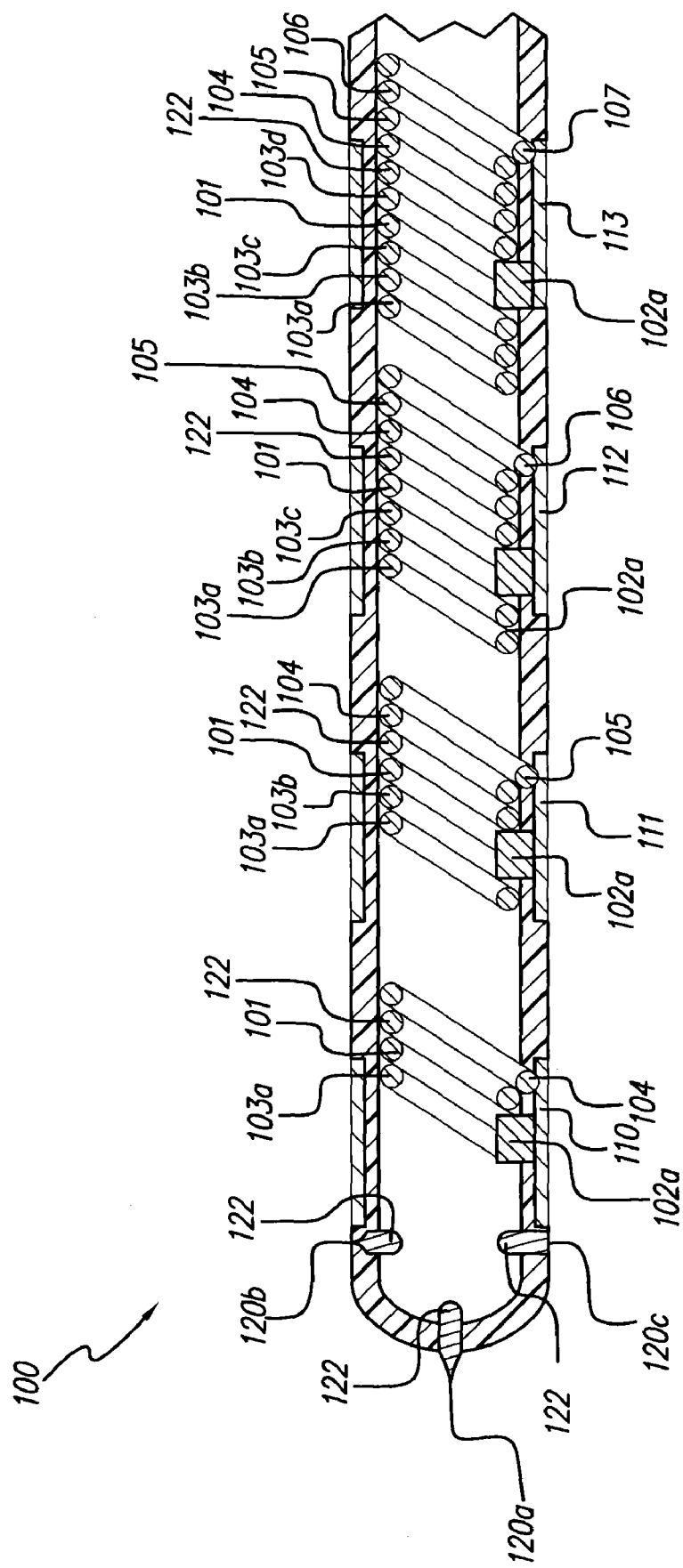
FIGS. 6A and 6B show, in axial cross-section view, the distal end of leads of the present invention, including multiple exemplary recording electrodes.
Figure 6B:
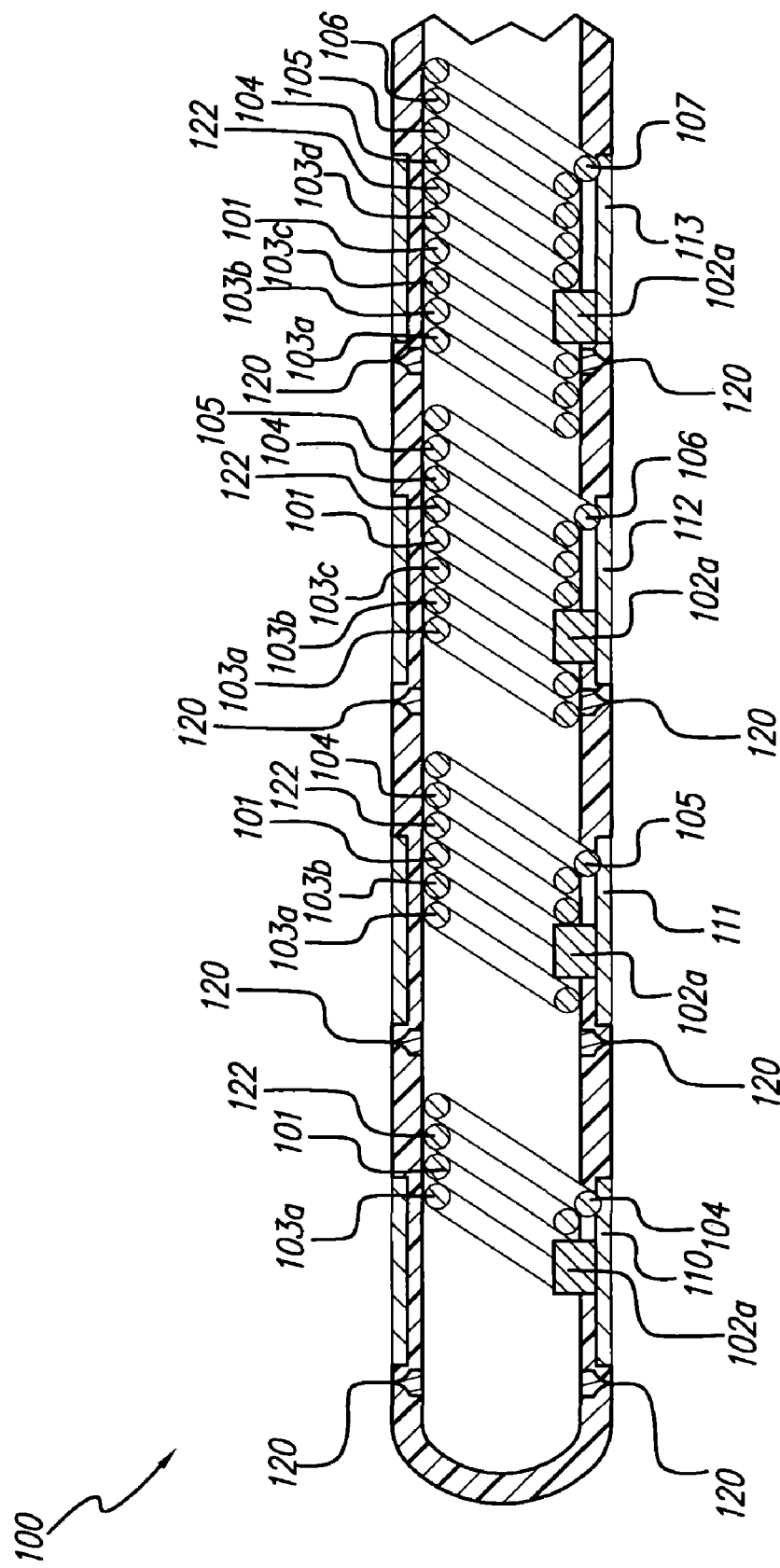

The lead could incorporate one or more microelectrodes or microwires (herein termed recording electrodes) for microelectrode recording, to help localize brain targets at single-neuron or multi-unit levels of resolution. The electrode(s) used for recording may be similar to those available from FHC Inc., of Bowdoinham, Me., USA. FIGS. 6A and 6B show leads including exemplary recording electrodes of the invention. (To facilitate describing the invention, a variety of configurations are shown in FIG. 6A. In practice, a lead may include only one of these recording electrodes or types of recording electrodes, while combinations are also possible.) For instance, a lead 100 as shown in FIG. 6A may include recording electrode 120*a*, 120*b*, and/or 120*c* (or the like) connected via wire 122 through lead 100 to a recording system. As shown in FIG. 6B, a series of recording electrodes 120 may be positioned on the lead, to record activity at a number of sites where stimulation and/or lesioning may occur. (The wires leading to the recording electrodes 120 are shown in FIG. 6A but not shown in FIG. 6B.)

Alternatively, stimulating/lesioning electrodes 110,111, 112,113 may be used for recording to determine the target(s). This may be more practical if sectioned electrodes, described earlier, are employed. The recording capability could record, e.g., EEG, field potentials, and/or evoked potentials for monitoring of seizures, localization of seizure foci, identification of motor or sensory activity, and/or identification of brain targets. Instead or in addition to recording capability, the lesioning target(s) may be chosen based on the clinical effects of stimulation. For instance, the electrode(s) through which stimulation produces optimal results with the least adverse effects (i.e., the best safety/efficacy profile) may be used to produce a lesion(s).

Systems useful with the brain stimulation leads of the invention including recording capability include those described in the following papers: Burgess R C, "Design and evolution of a system for long-term electroencephalographic and video monitoring of epilepsy patients" *Methods* 2001 October;25(2):231-48; Scott, et al., "Design of an intensive epilepsy monitoring unit" *Epilepsia* 2000;41 Suppl 5:S3-8; Bertram, at al., "Design and construction of a long-term continuous video-EEG monitoring unit for simultaneous recording of multiple small animals" *Brain Res Brain Res Protoc* 1997 Dec. 1;2(1):85-97; and Ives, et al., "128-channel cable-telemetry EEG recording system for long-term invasive monitoring" *Electroencephalogr Clin Neurophysiol* 1991 July;79(1):69-72.

Figure 7:
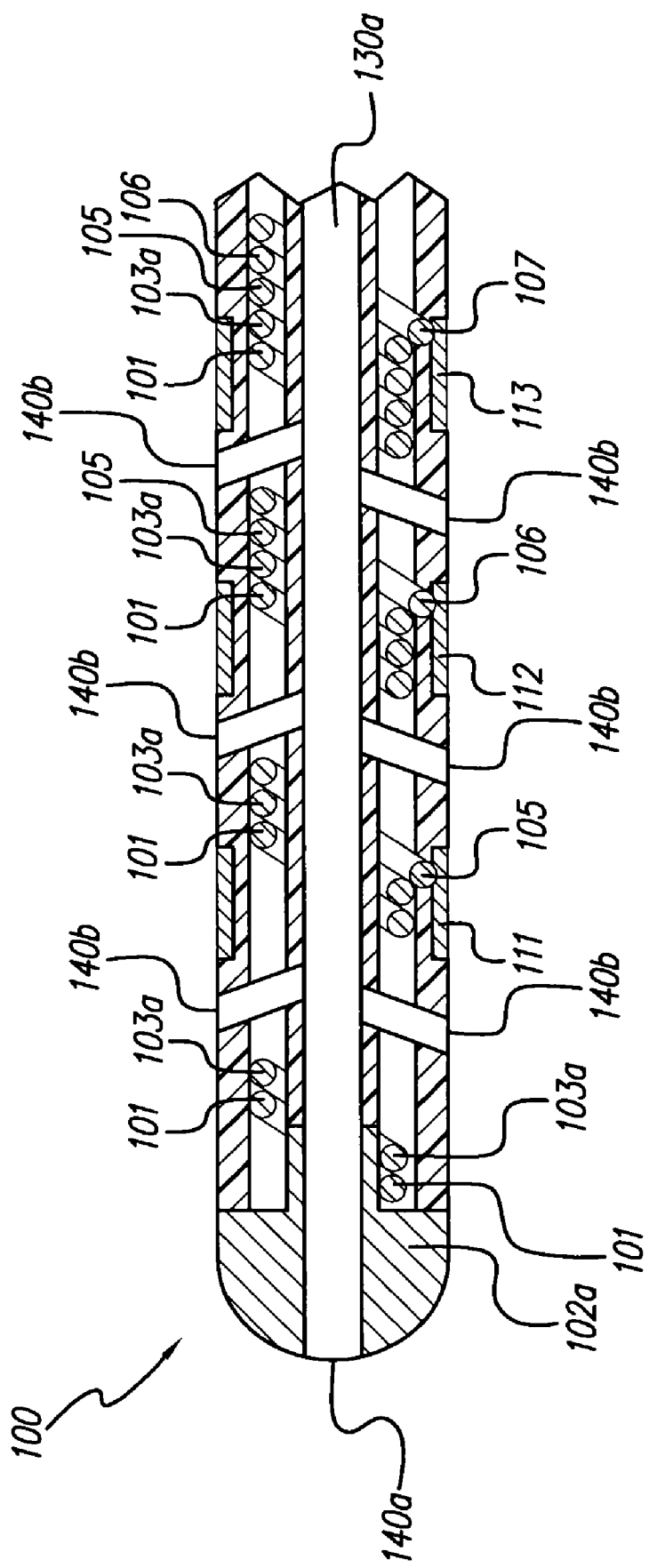
FIG. 7 is an axial cross-section view of the distal end of a lead of the present invention, including multiple exemplary infusion ports.
Figure 8A:
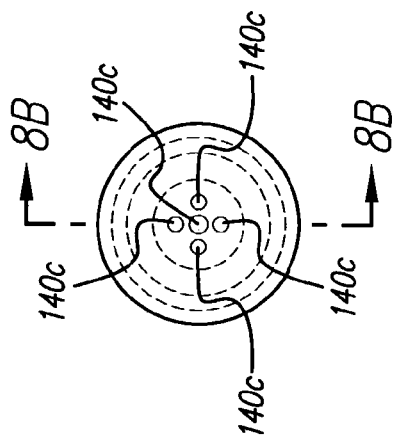
FIG. 8A is an end view of the distal end of a lead of the present invention, including multiple exemplary lumens and infusion ports.
Figure 8B:
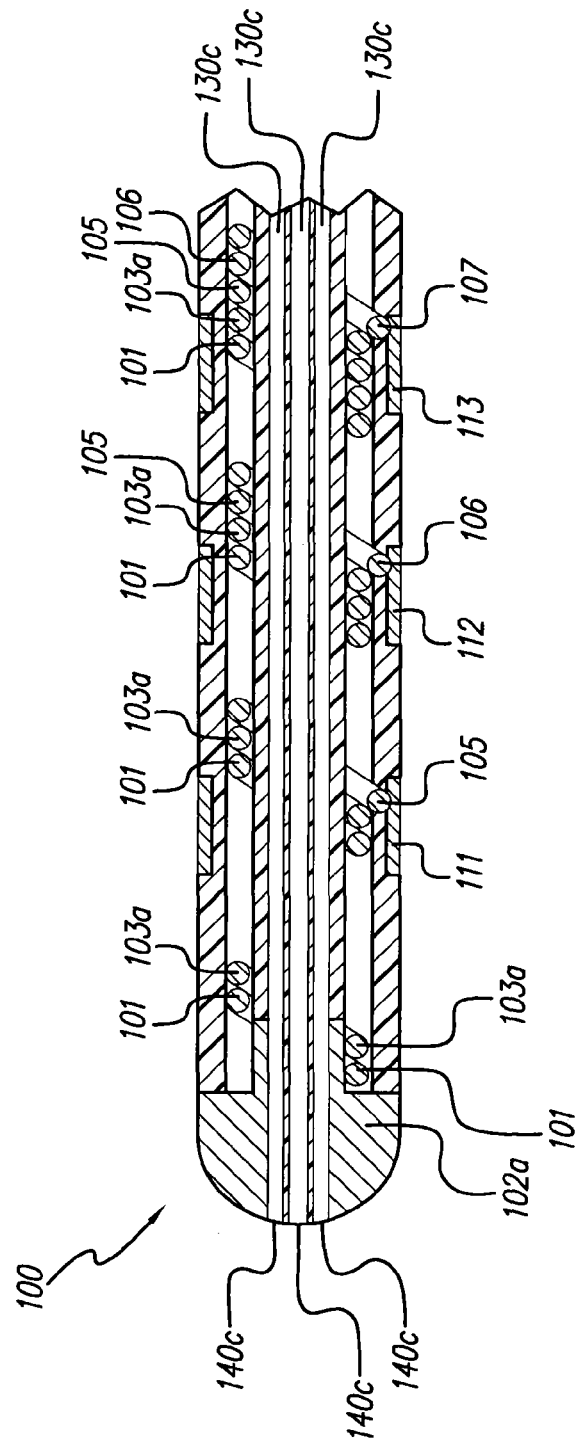
FIG. 8B is a partial cross-section taken along line 8B-8B of FIG. 8A.

In yet other embodiments, brain stimulation leads of the invention include one or more ports, enabling, for instance, drug delivery. For instance, FIG. 7 shows a lumen 130*a* extending through lead 100 and ending in a port 140*a*. FIG. 7 also shows optional side ports 140*b* branching from lumen 130*a* at various positions along lead 100. In another variation, FIGS. 8A and 8B show lumens 130*c* extending through lead 100 and ending in ports 140*c*. Although not shown in these drawings, side ports could also extend from lumens 130*c*. Lumen(s) and port(s) can serve as catheters to deliver substances that influence the activity of neural elements and circuits.

As examples, excitatory or inhibitory neurotransmitters and/or analogues, neurotrophic agents, and/or chemotherapuetic agents could be infused, either constantly or intermittently. Infusion could be provided by an infusion device on a contingency basis in response to a detected chemical or electrical cue from the local or a remote brain area. Infusion could also or instead by self-activated. For example, the patient could initiate a dose of seizure attenuating or suppressing drug delivered directly into the focus if he/she experienced an aura or felt tremor or other seizure warning. As another example, the stimulation or infusion capabilities may be as described in US patent application 2002/0013612 A1, or any of U.S. Pat. Nos. 6,356,784; 6,094,598; 5,832, 932; which application and patents are incorporated herein by reference.

The ability to use a stimulation lead for lesioning creates additional treatment options for DBS and other brain stimulation patients. For instance, in cases of infection or erosion, the brain stimulation lead can be used to create a lesion before removal of the system, thereby avoiding a separate procedure. In cases in which frequent battery changes are required, a lesion using the implanted lead can also be considered. Lesioning through implanted brain stimulation leads producing clinical benefit with stimulation could also be considered an alternative to chronic stimulation (even when surgical or other revisions are not required).

In addition, a lead can be used subacutely to create progressive, graduated lesions, inside or outside the operating room. For example, a lesioning lead intended for chronic implantation may be used. As another example, a brain stimulation lead with a temperature sensor(s), such as described earlier, may be used. The lead may be attached to an RF generator through a small incision to reveal the connector at the proximal end of the lead, or may attach via a percutaneous connector, or may receive power transcutaneously. For instance, the lead may have an RF coil (tuned via an in-line capacitor) inductively linked to the RF generator. Graded or incremental lesions made in several sessions over time may have advantages for some patients, for instance, patients with symptoms such as bradykinesia, rigidity, or dystonia, where response to lesioning may lag by several days, and/or patients limited by the appearance of acute side effects such as chorea during lesioning. In such patients, the lesions could later be repeated or expanded using the same or alternate electrodes, if clinically warranted. Creating a lesion over several sessions with a subacute or chronic lead helps ensure that the lesion is not made too large, thus reducing the risk of long-term side effects.

While the invention herein disclosed has been described by means of specific embodiments and applications thereof, numerous modifications and variations could be made thereto by those skilled in the art without departing from the scope of the invention set forth in the claims. For instance, as illustrated above, the invention is useful for treating patients with movement disorders, but may also be used in treating patients with other disorders. Other uses of the invention include, but are not limited to, treating patients with chronic pain, epilepsy, psychiatric disorders, and other disorders where stimulation, lesioning, and/or drug infusion are currently used or contemplated.

What is claimed is:

1. A method for creating a lesion in a patient's body, comprising:
    a) implanting a lead in a patients brain;
    b) electrically connecting the lead to an external RF generator;
    c) creating a lesion with the lead and the external RF generator;
    d) disconnecting the lead from the external RF generator;
    e) waiting at least one week;
    f) evaluating the results of the lesion; and
    g) repeating b) through f) at least once to create a progressive, graduated lesion.

2. The method of claim 1 further comprising connecting the lead to a pulse generating device and delivering stimulating pulses to the patient's brain with the lead and the pulse generating device.

3. The method of claim 1 further comprising removing the lead from the patient's brain.

4. The method of claim 1 further comprising creating the lesion outside the operating room.

5. The method of claim 1 wherein electrically connecting to and disconnecting the lead from the external RF generator comprises electrically connecting and disconnecting transcutaneously.

6. The method of claim 5 further comprising an RF coil coupled to the lead that is inductively coupled to the external RF generator.

7. The method of claim 1 wherein the lesion is created in response to a hardware complication requiring hardware revision or removal of one or more components of a brain stimulation system.

8. The method of claim 7 wherein the hardware complication comprises at least one of infection, erosion, fracture, migration, short-circuit, and physical disconnection of one or more components of a brain stimulation system.

9. The method of claim 1 wherein the lesion is created in response to the patient developing a tolerance to brain stimulation.

10. The method of claim 2 wherein the lesion is created in response to the patient developing a tolerance to brain stimulation.

11. The method of claim 1 wherein the lesion is created in response to failure of a battery in a brain stimulation system.

12. The method of claim 1 wherein the lesion is created in response to a need for frequent battery replacements in a brain stimulation system.

13. The method of claim 1 wherein the lesion is created in response to a need for progressively increasing current output from a brain stimulation system.

14. The method of claim 1 wherein the progressive, graduated lesion is created as an alternative to using brain stimulation.

15. The method of claim 1 wherein the progressive, graduated lesion is created as an addition to delivering stimulating pulses to the patient's brain with a pulse generating device.

16. The method of claim 15 wherein the progressive, graduated lesion is created prior to initiation or resumption of stimulation.

17. The method of claim 16 wherein the progressive, graduated lesion decreases the current delivery requirements of stimulation.

18. The method of claim 16 wherein the progressive, graduated lesion prolongs battery life of the pulse generating device.

19. The method of claim 2 wherein the progressive, graduated lesion prolongs battery life of the pulse generating device.

* * * * *